(12) United States Patent
McArthur et al.

(10) Patent No.: US 7,530,970 B2
(45) Date of Patent: May 12, 2009

(54) INFLATION SYRINGE QUICK RELEASE APPARATUS

(75) Inventors: Gregory R. McArthur, Sandy, UT (US); Fred P. Lampropoulos, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 404 days.

(21) Appl. No.: 10/998,382

(22) Filed: Nov. 29, 2004

(65) Prior Publication Data

US 2006/0129107 A1 Jun. 15, 2006

(51) Int. Cl.
*A61M 5/00* (2006.01)
(52) U.S. Cl. .................. 604/208; 604/97.01; 604/207; 604/211
(58) Field of Classification Search ............. 604/96.01, 604/97.01, 97.02, 98.01, 99.01, 100.01, 100.03, 604/920, 187, 207–211, 218, 221, 224; 606/192, 606/108, 191; 600/431–432
See application file for complete search history.

(56) References Cited

U.S. PATENT DOCUMENTS

| 4,832,692 | A | * | 5/1989 | Box et al. ................. 604/99.01 |
| 6,063,057 | A | * | 5/2000 | Choh ....................... 604/99.01 |
| 6,106,496 | A | * | 8/2000 | Arnissolle ................ 604/97.01 |
| 6,599,293 | B2 | * | 7/2003 | Tague et al. .................... 606/94 |

* cited by examiner

*Primary Examiner*—Nicholas D Lucchesi
*Assistant Examiner*—Quynh-Nhu H Vu
(74) *Attorney, Agent, or Firm*—Ryan D. Benson; Stoel Rives, LLP (57) ABSTRACT

The present invention relates to a collar for use with an inflation device, the collar having a release mechanism allowing a user to advance and/or retract a plunger in a non-threaded fashion. According to one embodiment of the present invention, the release mechanism has a first position in which the plunger is threadably engaged and a second position in which the plunger can be advanced and/or retracted in a non-threaded fashion. In one embodiment the release mechanism includes a displaceable member and an engagement mechanism. In another embodiment, the release mechanism is utilized with a sleeve which allows the collar to be decoupled from the inflation device by rotation of the collar.

27 Claims, 9 Drawing Sheets

INFLATION SYRINGE QUICK RELEASE APPARATUS

BACKGROUND OF THE INVENTION

1. The Field of the Invention

The present invention relates to a collar for use with an inflation device. More particularly, the present invention relates to a collar having a release mechanism that allows a user to advance and/or retract a plunger in a non-thread fashion.

2. The Relevant Technology

Inflation mechanisms are widely utilized in catheterization procedures to perform specified functions. For example, inflation devices can be utilized with specialized balloon apparatuses to open arterial blockages or perform similar procedures. Typically such inflation devices include a syringe and a plunger disposed within the barrel of the syringe. A practitioner advances the plunger to increase the atmospheric pressure within the syringe and the connected balloon to inflate the balloon to a desired size and/or degree of pressurization. Typically, such plungers are attached to the syringe barrel in a threaded fashion to allow for controlled and incremental movement of the plunger relative to the barrel of the syringe.

While the threaded configuration of the plunger allows for controlled and incremental movement of the plunger relative to the barrel of the syringe, under some circumstances it is desirable that the practitioner be able to advance or retract the plunger more quickly than that allowed by incremental threaded movement of the plunger. A number of different types and configurations of release mechanisms have been utilized to allow the user to advance/retract the plunger in a non-threaded fashion. One such apparatus comprises a collar coupled to the distal portion of the syringe. The collar allows the user to advance/retract the plunger in a non-threaded fashion by simply decoupling the collar from the distal end of the plunger barrel.

When the collar is coupled to the syringe, the threads of the plunger threadably interact with the collar to allow for advancement or retraction of the plunger by rotation of the plunger. When the collar is decoupled from the syringe, the position of the plunger relative to the syringe can be quickly changed by sliding the collar and plunger in a reward direction. To advance the plunger, the collar is moved toward the back of the plunger by spinning the collar while the plunger remains in a fixed position relative to the barrel of the syringe. This moves the collar in a rearward direction allowing the user to advance the plunger in a non-threaded fashion without requiring rotational movement of the plunger itself. The user can then recouple the collar to the distal end of the barrel of the syringe and resume threaded movement of the plunger in the incremental and controlled fashion previously utilized.

BRIEF SUMMARY OF THE INVENTION

The present invention relates to a collar for use with an inflation device. More particularly, the present invention relates to a collar having a release mechanism allowing a user to advance and/or retract a plunger in a non-threaded fashion. According to one embodiment of the present invention, the release mechanism has a first position in which the plunger is threadably engaged and a second position in which the plunger can be advanced and/or retracted in a non-threaded fashion.

In one embodiment the release mechanism includes a displaceable member and an engagement mechanism. The displaceable member cooperatively interacts with the engagement mechanism such that the engagement mechanism selectively engages and releases the plunger. When the displaceable member is in a first position the displaceable member engages the engagement mechanism along a horizontal plane. In a second position, the displaceable member engages the engagement mechanism utilizing one or more ramp surfaces. In one embodiment, the engagement mechanism engages a plunger having a plurality of threads.

In another embodiment, the collar includes both a release mechanism and a coupler mechanism. The release mechanism allows the user to advance/retract the plunger in a non-threaded fashion. The coupler mechanism allows the collar to be decoupled from the inflation device. The combination of the release mechanism and the coupler mechanism provides additional functionality not realized by utilizing a release mechanism alone. For example, the release mechanism/coupler mechanism combination can be utilized with a contrast media injection syringe or other syringe in which the syringe is filled with fluids or other materials. The coupler mechanism allows the user to remove the collar and/or the plunger in order to back fill the syringe with desired fluids or other materials. The collar and/or the plunger can then be recoupled to the syringe. Once the collar is recoupled to the syringe, the release mechanism can be utilized to advance the plunger to a desired position. Once the plunger is in the desired position, the practitioner can incrementally advance and/or retract the plunger in a threaded fashion by rotating the plunger relative to the syringe barrel.

In one embodiment, the present invention relates to a release mechanism having one-handed operability. In another embodiment, the present invention relates to a method of utilizing a coupler mechanism in combination with a release mechanism relative to a syringe device. In another embodiment, the present invention relates to a method of manufacturing a release mechanism having horizontal portions and one or more ramp surfaces. Engagement or disengagement of the plunger is controlled by the positioning of the horizontal portions and the one or more ramps surfaces of the components of the release mechanism.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The present invention relates to a collar for use with an inflation device. In particular, the present invention relates to a collar having a release mechanism allowing a user to advance and/or retract a plunger in a non-threaded fashion. According to one embodiment of the present invention, the release mechanism has a first position in which the plunger is threadably engaged and a second position in which the plunger can be advanced and/or retracted in a non-threaded fashion.

In one embodiment the release mechanism includes a displaceable member and an engagement mechanism. The displaceable member cooperatively interacts with the engagement mechanism such that the engagement mechanism selectively engages and releases the plunger. When the displaceable member is in a first position the displaceable member engages the engagement mechanism along a horizontal plane. In a second position, the displaceable member engages the engagement mechanism utilizing one or more ramp surfaces. In one embodiment, the engagement mechanism engages a plunger having a plurality of threads.

In another embodiment, the collar includes both a release mechanism and a coupler mechanism. The release mechanism allows the user to advance/retract the plunger in a non-threaded fashion. The coupler mechanism allows the collar to be decoupled from the inflation device. The combination of the release mechanism and the coupler mechanism provides additional functionality not realized by utilizing a release mechanism alone. For example, the release mechanism/coupler mechanism combination can be utilized with a contrast media injection syringe or other syringe in which the syringe is filled with fluids or other materials. The coupler mechanism allows the user to remove the collar and/or the plunger in order to back fill the syringe with desired fluids or other materials. The collar and/or the plunger can then be recoupled to the syringe. Once the collar is recoupled to the syringe, the release mechanism can be utilized to advance the plunger to a desired position. Once the plunger is in the desired position, the practitioner can incrementally advance and/or retract the plunger in a threaded fashion by rotating the plunger relative to the syringe barrel.

In one embodiment, the present invention relates to a release mechanism having one-handed operability. In another embodiment, the present invention relates to a method of utilizing a coupler mechanism in combination with a release mechanism relative to a syringe device. In another embodiment, the present invention relates to a method of manufacturing a release mechanism having horizontal portions and one or more ramp surfaces. Engagement or disengagement of the plunger is controlled by the positioning of the horizontal portions and the one or more ramps surfaces of the components of the release mechanism.

Figure 1:
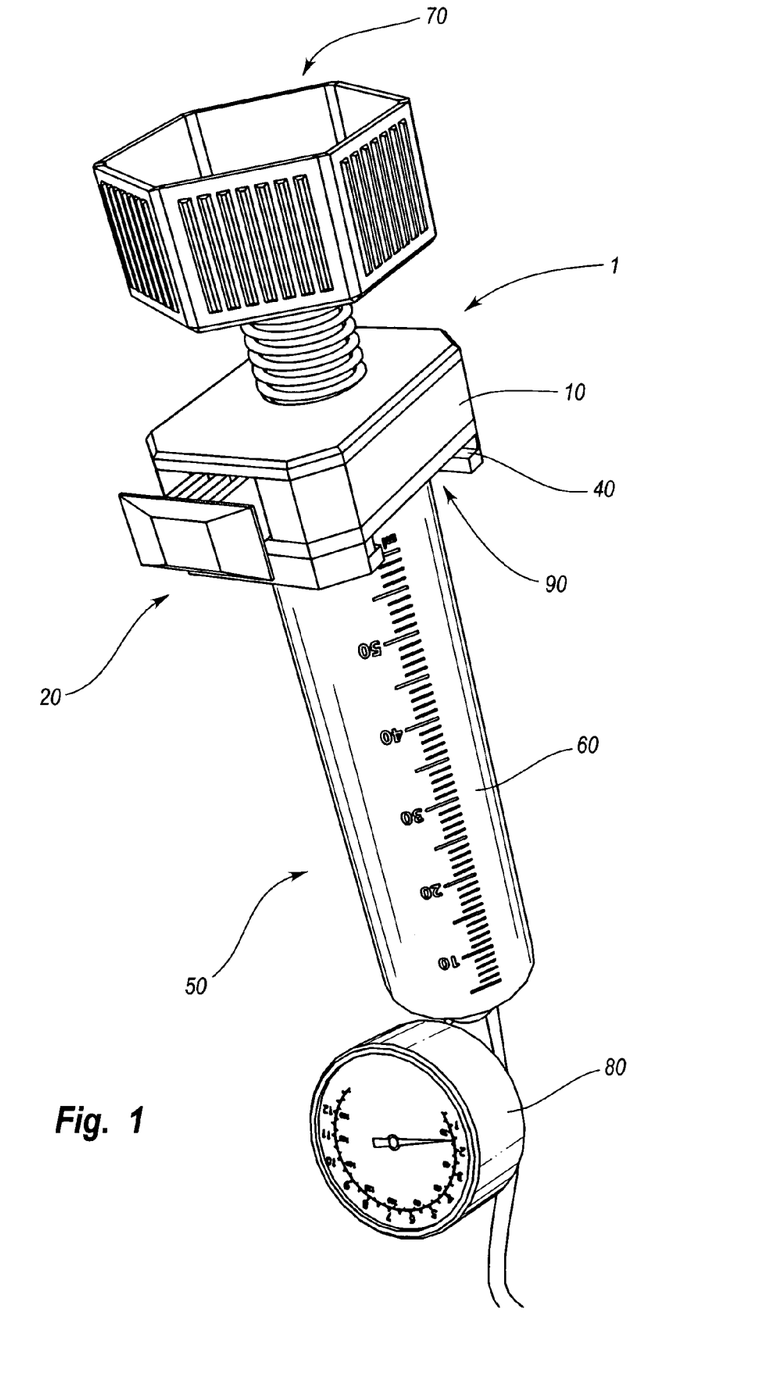
FIG. 1 illustrates a collar having a release mechanism coupled to a syringe apparatus according to one embodiment of the present invention.

FIG. 1 is a perspective view of a collar 1 coupled to a syringe 50 according to one embodiment of the present invention. In the illustrated embodiment, collar 1 includes a housing 10, a release mechanism 20, and a sleeve 40. Syringe 50 includes a barrel 60, a plunger 70, a pressure gauge 80, and a flange 90. Housing 10 comprises the body of collar 1 and provides a mechanism for securing the other components of collar 1.

Release mechanism 20 is positioned, at least in part, inside housing 10. Release mechanism 20 provides a mechanism allowing the user to advance or retract the plunger in a non-threaded fashion. Sleeve 40 is coupled to housing 10 of collar 1. Sleeve 40 provides a mechanism for selectively coupling collar 1 to syringe 50. In the illustrated embodiment, sleeve 40 is coupled to a flange 90 of syringe 50 at the proximal end of barrel 60. Sleeve 40 allows collar 1 to be decoupled from syringe 50 by simply rotating collar 1. Sleeve 40 is one example of a coupler mechanism which allows the collar to be decoupled from the syringe.

Syringe 50 can be utilized to inject, retract, inflate, or otherwise be utilized in procedures requiring the introduction or withdrawal of liquids, gases or materials for use in medical procedures. In the illustrated embodiment, syringe 50 comprises an inflation device. Syringe 50 includes a plunger 70, a pressure gauge 80, a barrel 60, and a flange 90. Plunger 70 is disposed within syringe 50 to expel or to draw liquids, gases and/or other materials into or out of syringe 50. Barrel 60 provides a reservoir for holding liquids, gases and/or other materials to be expelled from syringe 50. The distal end of plunger 70 is disposed within barrel 60. Plunger 70 is threadably coupled to collar 1 in a selective fashion allowing plunger 70 to be advanced or retracted in both a threaded and a non-threaded fashion. Release mechanism 20 allows the user to select between engagement and non-engagement of plunger 70.

Pressure gauge 80 is linked to barrel 60 of syringe 50. Pressure gauge 80 provides and indication of the internal pressure within barrel 60. This allows the user to monitor and control the desired amount of pressurization as may be required for individualized procedures. Flange 90 is coupled to barrel 60 at the proximal end of syringe 50. Flange 90 provides a mechanism allowing sleeve 40 to be coupled to syringe 50. As will be appreciated by those skilled in the art, a variety of types and configurations of collars and release mechanisms can be utilized without departing from the scope and spirit of the present invention. Additionally, the collars and release mechanisms can be utilized with a variety of different types and configurations of syringes utilizing a variety of types and configurations of coupling mechanisms without departing from the scope and spirit of the present invention. For example, in one embodiment the collar is utilized with a syringe for injecting fluids into the patient. In another embodiment, the release mechanism is positioned on the top rather than to the side of the housing. In another embodiment, the collar is integrally coupled to a syringe. In another embodiment, the plunger is threadably coupled directly to a syringe and the release mechanism of the collar allows the user to advance/retract the plunger in a non-threaded fashion.

Figures 2A, 2B:
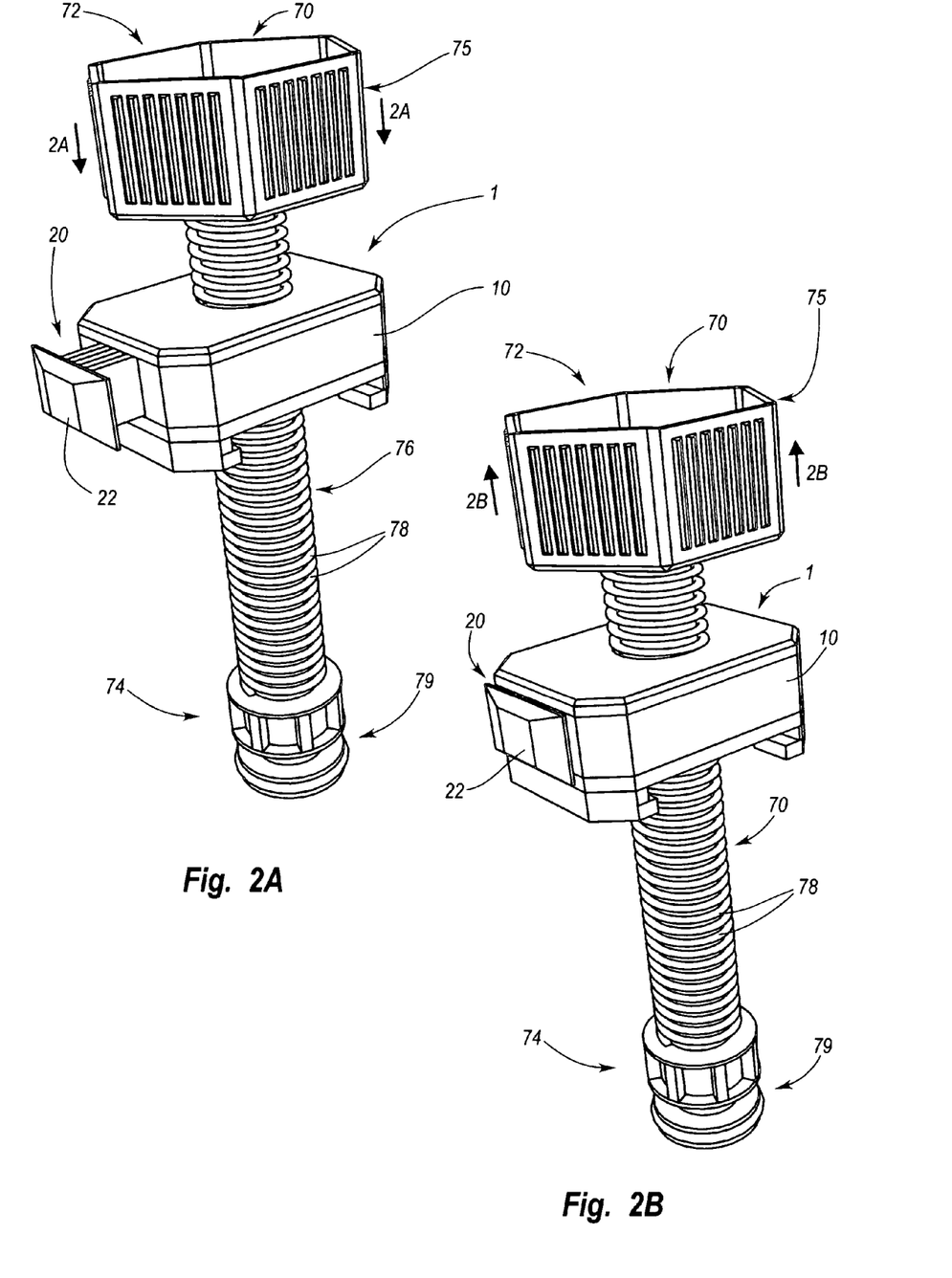
FIG. 2A illustrates the collar of FIG. 1 having a release mechanism in which the plunger is being advanced in a threaded fashion according to one embodiment of the present invention.
FIG. 2B illustrates the collar of FIG. 1 having a release mechanism wherein the plunger is retracted in a non-threaded fashion according to one embodiment of the present invention.

FIG. 2A is a perspective view of collar 1 and release mechanism 20 according to one embodiment of the present invention. Plunger 70 is positioned through the middle of collar 1. In the illustrated embodiment, plunger 70 includes a proximal end 72, a distal end 74, a graspable portion 75, a shaft 76, threads 78, and a barrel engagement portion 79. Proximal end 72 of plunger 70 is positioned above collar 2 opposite the barrel of the syringe with which plunger 70 is utilized. Distal end 74 of plunger 70 is configured to be positioned within the barrel of a syringe.

Graspable portion 75 is positioned at the proximal end 72 of plunger 70. Graspable portion 75 includes finger grips allowing the user to rotate plunger 70 during threaded manipulation of plunger 70 while also allowing the user to advance/retract plunger 70 in a non-threaded fashion. Shaft 76 is positioned proximally to graspable portion 75. Shaft 76 includes a plurality of threads 78 which interact with a movable portion of collar 1. The configuration of shaft 76 and threads 78 allows the user to control movement of plunger 70 and the position of a barrel engagement portion 79 within the barrel of the syringe.

When plunger 70 is threadably coupled to collar 1, the user twists graspable portion 75 to rotate shaft 76 and threads 78 to advance or retract plunger 70 in a threaded fashion. By allowing plunger 70 to be advanced and/or retracted in a threaded fashion, collar 1 provides for incremental and controlled movement of plunger 70 and thus barrel engagement portion 79 within the barrel of the syringe. Advancement of barrel engagement portion 79 regulates the pressurization within the syringe and/or movement of fluids, gases and/or other materials into or out of the barrel of the syringe in a controlled and precise manner.

Release mechanism 20 includes a button portion 22. Button portion 22 is positioned on the side and slightly protruding from the main body of collar 1. The position of the button portion 22 relative to collar 1 allows the user to actuate release mechanism 20 in a one-handed fashion. This allows the user to hold the syringe with the same hand that the user actuates the release mechanism 20. As a result, the user can utilize the other hand to perform other aspects of a medical or other procedure. For example, the user can manipulate the position of a balloon catheter or advance and retract the plunger while manipulating button portion 22.

In the illustrated embodiment, button portion 22 is in a non-depressed configuration. When button portion 22 is in a non-depressed configuration, release mechanism 20 allows the user to advance or retract plunger 70 in a threaded fashion. In the illustrated embodiment, directional arrows 2a-2a illustrate the directional movement of plunger 70 as plunger 70 is being advanced. As will be appreciated, the directional forward directional movement indicated by directional arrows 2a-2a occurs in connection with rotation of plunger 70. When plunger 70 is advanced, barrel engagement portion 79 is advanced in a distal direction through barrel 60 of syringe 50 (See FIG. 1). As barrel engagement portion 79 advances in a distal direction, the effective capacity of the barrel for holding fluids, gases, and the like is reduced. When the barrel is filled with a liquid or a gas, advancement of barrel engagement portion 79 can result in expelling of the liquid or gas and/or pressurization of the liquid or gas within the barrel. As will be appreciated by those skilled in the art, plunger 70 can be retracted in the same threaded fashion in which the plunger is advanced in FIG. 2A.

FIG. 2B is a perspective view of collar 1 utilized in connection with plunger 70. In the illustrated embodiment, button portion 22 is in a depressed configuration. When button portion 22 is in a depressed configuration, release mechanism 20 allows the user to advance/retract plunger in a non-threaded fashion. In the illustrated embodiment, directional arrows 2b-2b illustrate the directional movement of plunger 70 as plunger 70 is retracted. When plunger 70 is retracted, barrel engagement portion 79 moves in a proximal direction relative to the barrel of the syringe. When barrel engagement portion 79 moves in a proximal direction, the effective volume of the barrel for holding fluids, gases and/or other materials is increased. As the effective volume of the barrel increases, liquids, gases and/or materials can be drawn into the barrel or the pressurization of the air in the barrel can be reduced.

By permitting plunger 70 to be advanced or retracted in a non-threaded fashion, release mechanism 20 allows the user to quickly and efficiently effectuate a large amount of displacement of barrel engagement portion 79. Large amounts of displacement of barrel engagement portion 79 facilitates efficient and desirable expulsion or retraction of gases and/or fluids into or out of the syringe during a procedure. For example, the user can advance the syringe to a desired position at the beginning of an operation to be performed. For example, where the syringe is utilized to inject contrast media the user can advance plunger 70 to eliminate air or other gases within the barrel before injecting the contrast media fluid into the patient.

Collar 1 and release mechanism 20 allows the practitioner to advance and/or retract plunger 70 quickly to achieve an initial desired degree of pressurization within the inflation device. When the button portion 22 of release mechanism 20 is not in a depressed configuration, the user can advance or retract plunger 70 in a threaded fashion, by rotating plunger 70 relative to barrel 60, to provide for incremental and controlled movement of barrel engagement portion 79 within the barrel. As will be appreciated by those skilled in the art, plunger 70 can be advanced in the same non-threaded fashion in which the plunger is advanced in FIG. 2A.

Figure 3:
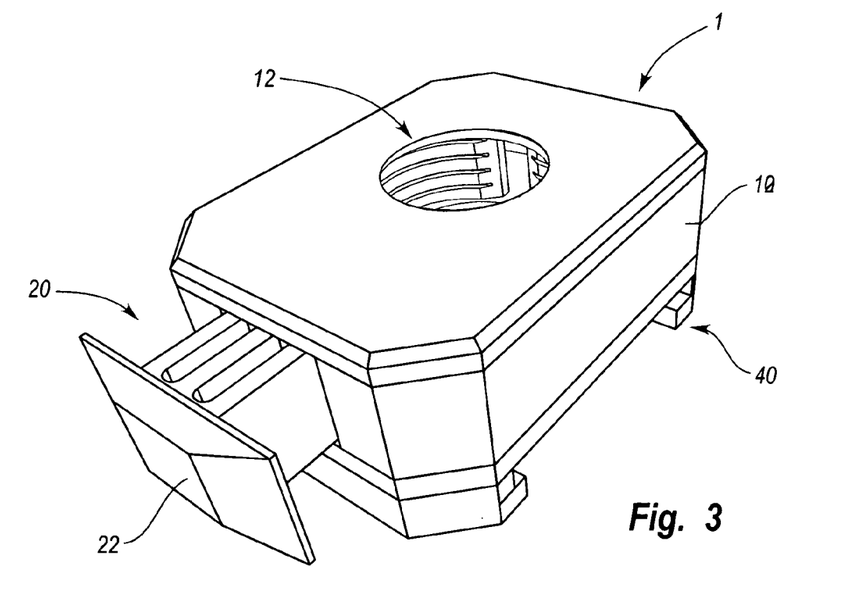
FIG. 3 illustrates the collar of FIG. 1 having a release mechanism shown in the absence of a plunger according to one embodiment of the present invention.

FIG. 3 is a perspective view of collar 1 according to one embodiment of the present invention. In the illustrated embodiment, collar 1 includes a housing 10, a release mechanism 20, and a sleeve 40. Housing 10 includes an aperture 12. Aperture 12 is adapted to accommodate plunger 70 illustrated in FIGS. 2A and 2B. Housing 10 provides a mechanism for securing the components of collar 1. Aperture 12 is configured such that it can accommodate the plunger in a threaded or non-threaded fashion. As previously discussed, release mechanism 20 allows the user to select whether the plunger is engaged by aperture 12 in a threaded or non-threaded fashion.

As will be appreciated by those skilled in the art, a variety of types and configurations of providing selective threaded or non-threaded engagement of the plunger can be utilized without departing from the scope and spirit of the present invention. For example in one embodiment, the release mechanism threadably or non-threadably engages the plunger. An example of a release mechanism that allows threaded or non-threaded engagement of the plunger is illustrated in FIGS. 3-6C.

Figure 4:
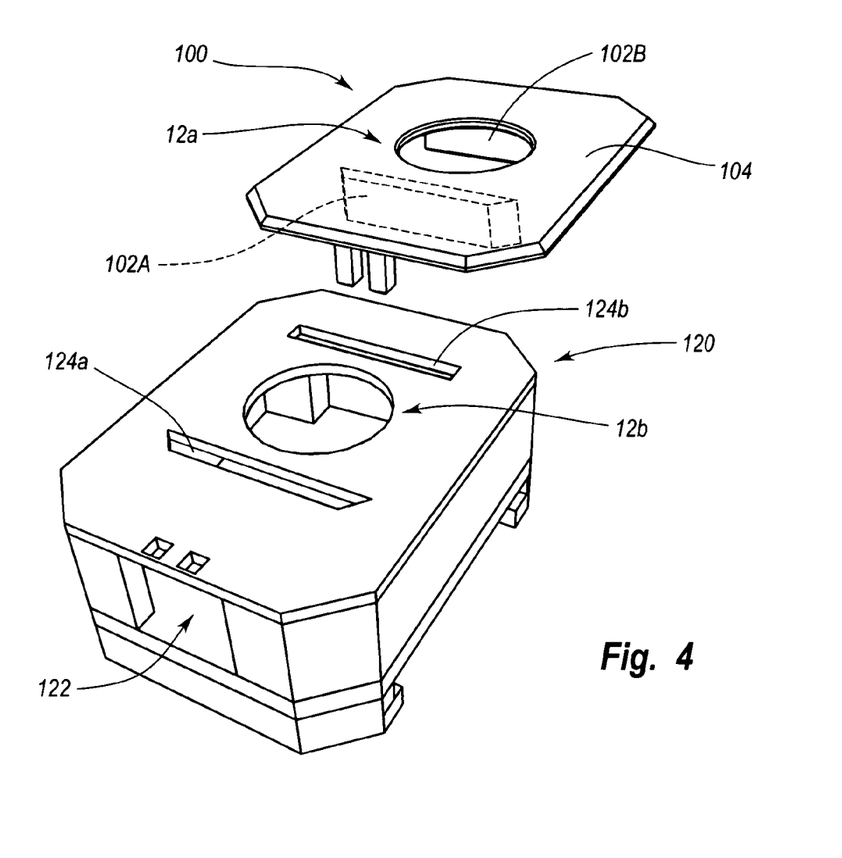
FIG. 4 is a partial exploded view illustrating a cap member and a housing main body of the collar, according to one embodiment of the present invention.

FIG. 4 is a partial exploded view of housing 10 according to one embodiment of the present invention. In the illustrated embodiment, housing 10 comprises a cap member 100 and a housing main body 120. In the illustrated embodiment, aperture 12 comprises a first portion 12a positioned in cap member 100 and a second portion 12b positioned in housing main body 120. First portion 12a and second portion 12b accommodate the shaft of the plunger as illustrated in FIGS. 2A and 2B.

In the illustrated embodiment, cap member 100 is configured to be coupled to housing main body 120. Cap member 100 includes a first projection 102a, a second projection 102b, and a top surface 104. First projection 102a and second projection 102b facilitate coupling of cap member 100 to housing main body 120. Additionally, first projection 102a and second projection 102b facilitate proper operation of the release mechanism as will be discussed in greater detail with reference to FIG. 6A and FIG. 6B. Top surface 104 of cap member 100 provides a uniform surface that is configured to cover the top of housing main body 120.

Housing main body 120 provides a structure on which the other portions of collar 1 can be secured. Housing main body 120 includes a release mechanism void 122, a first projection slot 124a, and a second projection slot 124b. Release mechanism void 122 is positioned in the internal portion of housing main body 120. Release mechanism void 122 is configured to accommodate release mechanism 20 (see FIG. 5.) First projection slot 124a and second projection slot 124b are positioned on the upper surface of housing main body 120. First projection slot 124a is configured to accommodate first projection 102a of cap member 100. Second projection slot 124b is configured to accommodate second projection 102b of cap member 100. The configuration of first projection slot 124a and second projection slot 124b also facilitates proper positioning of first projection 102a and second projection 102b relative to the components of release mechanism 20 as will be illustrated in greater detail with reference to FIGS. 6A-6C.

Figure 5:
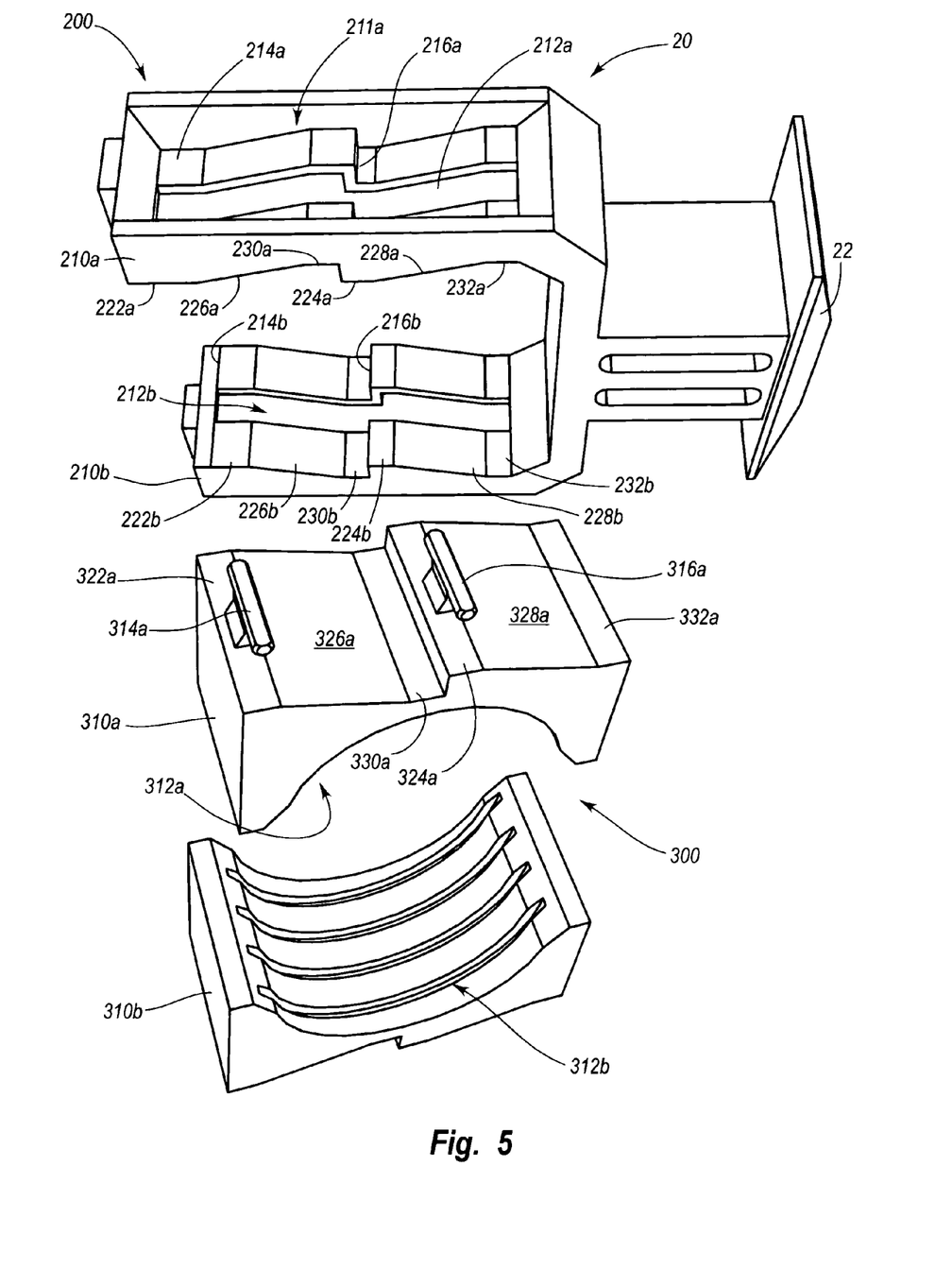
FIG. 5 is an exploded view illustrating a displaceable member and an engagement mechanism of the release mechanism according to one embodiment of the present invention.

FIG. 5 is an exploded view of release mechanism 20 illustrating a displaceable member 200 and an engagement mechanism 300. In the illustrated embodiment, release mechanism 20 includes a button portion 22. Button portion 22 allows a user to actuate release mechanism 20 to selectively advance or retract the plunger in a non-threaded fashion. In the illustrated embodiment, button portion 22 is actuated by being depressed when contacted by the user. When the user depresses button portion 22, the plunger is no longer threadably engaged by the collar and the plunger can be moved in a non-threaded fashion.

In the illustrated embodiment, release mechanism 20 comprises a displaceable member 200 and an engagement mechanism 300. In the illustrated embodiment, displaceable member 200 includes a first component 210a and a second component 210b. Similarly engagement mechanism 300 includes a first component 310a and a second component 310b. First component 310a and second component 310b of engagement mechanism 300 are configured to be positioned between first component 210a and second component 210b of displaceable member 200. First component 210a and second component 210b interact with first component 310a and second component 310b to selectively engage and disengage the plunger, thereby allowing the user to advance/retract the plunger in both non-threaded and threaded fashion.

As previously discussed, depression of button portion 22 disengages the threaded coupling of the collar and the plunger. Depression of button portion 22 results in movement of displaceable member 200. The juxtaposition of the components of displaceable member 200 relative to the components of engagement mechanism 300 during depression of button portion 22 will be discussed in greater detail with reference to FIGS. 6A-6C. In the illustrated embodiment, first component 210a includes a recess 211a, a slot 212a, a flange member void 214a, and a flange member void 216a.

First component 310a of engagement mechanism 300 includes a flange member 314a and a flange member 316a. Recess 211a is configured to accommodate flange member 314a and flange member 316a. The width of recess 211a is configured to allow for movement of first component 210a and displaceable member 200 relative to flange members 314a and 316a and first component 310a without obstructing the head of flange member 314a and flange member 316a. Slot 212a is positioned along the length of recess 211a. Slot 212a allows for movement of flange member 314a and flange member 316a without obstructing the upright base of flange member 314a and flange member 316a. More specifically, slot 212a is narrower than recess 211a to accommodate the upright base of flange member 314a and flange member 316a while preventing the passage of the head of flange member 314a and flange member 316a through slot 212a. Flange member void 214a allows flange member 314a to be positioned in recess 211a during assembly of release mechanism 20. Similarly, flange member void 216a allows flange member 316a to be properly positioned in recess 211a during assembly of release mechanism 20. The juxtaposition of the components of displaceable member 200 and engagement mechanism 300 will be discussed in greater detail with reference to FIG. 6A and FIG. 6B.

In the illustrated embodiment, second component 210b includes a recess 211b, a slot 212b, a flange member void 214b, and a flange member void 216b. For the sake of simplicity, the discussion of recess 211b and its relief surface will be discussed though such components are not clearly shown in FIG. 5. While recess 211b is not clearly shown in FIG. 5, it will be understood that the configuration of recess 211b relative to second component 210b mirrors the configuration of recess 211a relative to first component 210a.

Second component 310b of engagement mechanism 300 includes a flange member 314b and a flange member 316b. While the flange members 314b and 316b are not clearly shown in FIG. 5, it will be understood that flange members 314b and 316b closely mirror flange members 314a and 316 in form and function. Flange members 314b and 316b will be discussed in relation to recess 211b for the sake of clarity and to more fully address the features of second component 310b. Recess 211b is configured to accommodate flange member 314b and flange member 316b. The width of recess 211b is configured to allow for movement of second component 210b and displaceable member 200 relative to flange members 314b and 316b (see FIG. 6A) and second component 310b of engagement mechanism 300 without obstructing the head of the flange member 314b and flange member 316b (see FIG. 6A). Slot 212b is positioned along the length of recess 211b. Slot 212b allows for movement of flange member 314b and flange member 316b without obstructing the upright base of flange member 314b and flange member 316b (see FIG. 6A). In more particular, slot 212b is narrower than recess 211b to accommodate the upright base of flange member 314b and flange member 316b while preventing the passage of the head of flange member 314b and flange member 316b through slot 212b (see FIG. 6A).

Flange member void 214b allows flange member 314b to be positioned in recess 211b during assembly of release mechanism 20. Similarly, flange member void 216b allows flange member 316b to be properly positioned in recess 211b during assembly of release mechanism 20. As will be discussed in greater detail with reference to FIG. 6A and FIG. 6B.

As button portion 22 is depressed, displaceable member 200 is displaced relative to first component 310a and second component 310b of engagement mechanism 300. The configuration of recess 211a and slot 212a slidably secures flange member 314a and flange member 316a. This maintains engagement between first component 310a and first component 210a while also allowing free movement of first component 210a relative to first component 310a.

As first component 210a slides relative to flange member 314a and flange member 316a, the head of flange member 314a and flange member 316a maintains contact with recess 211a. In the illustrated embodiment, the surface of recess 211a that contacts the head of flange member 314a and flange member 316a comprises a relief surface including upper horizontal contact surfaces, ramp surfaces, and lower horizontal contact surfaces. As first component 210a moves relative to first component 310a flange member 314a maintains contact with relief surfaces of recess 211a. This maintains a desired degree of coupling between the contact surfaces of first component 210a and the contact surfaces of first component 310a.

In the illustrated embodiment, first component 210a includes a plurality of contact surfaces that are configured to be positioned adjacent the contact surfaces of first component 310a. In the illustrated embodiment, the contact surfaces of first component 210a include an upper horizontal contact surface 222a, an upper horizontal contact surface 224a, a first ramp surface 226a, a second ramp surface 228a, a lower horizontal contact surface 230a, a lower horizontal contact surface 232a, and a stop surface 240a. The contact surfaces of first component 310a include an upper horizontal contact surface 322a, an upper horizontal contact surface 324a, a first ramp surface 326a, a second ramp surface 328a, a lower horizontal contact surface 330a, and a lower horizontal contact surface 332a.

In the illustrated embodiment, second component 210b includes a plurality of contact surfaces that are configured to be positioned adjacent the contact surfaces of second component 310b. In the illustrated embodiment, the contact surfaces of second component 210b include an upper horizontal contact surface 222b, an upper horizontal contact surface 224b, a first ramp surface 226b, a second ramp surface 228b, a lower horizontal contact surface 230b, a lower horizontal contact surface 232b, and a stop surface 240b.

The contact surfaces of second component 310b include an upper horizontal contact surface 322b, an upper horizontal contact surface 324b, a first ramp surface 326b, a second ramp surface 328b, a lower horizontal contact surface 330b, and a lower horizontal contact surface 332b. Though the contact surfaces of second component 310b are not clearly shown in FIG. 5, the surfaces of second component 310b will be discussed with their corresponding reference numerals for the sake of simplicity and to more clearly describe the invention. It will be understood that the configuration of surfaces 322b, 326b, 328b, 330b, and 332b relative to second component 310b mirror the configuration of surfaces 322a, 326a, 328a, 330a, and 332a relative to first component 310a.

The contact surfaces of first component 210a and the contact surfaces of first component 310a facilitate lateral movement of first component 310a to cause separation of first component 310a from second component 310b. Similarly, the contact surfaces of second component 210b and the contact surfaces of second component 310b facilitate lateral movement of second component 310b to cause separation of second component 310b from first component 310a. Separation between first component 310a and second component 310b occurs when button portion 22 is depressed moving displaceable member 200 relative to first component 310a and second component 310b. This results in a sufficient degree of separation between first component 310a and second component 310b such that plunger engagement surface 312a and plunger engagement surface 312b no longer threadably engage threads 58 of plunger 50 allowing a user to advance/retract the plunger in a non-threaded fashion.

Additionally, the contact surfaces of first component 210a and first component 310a result in lateral movement of first component 310a in the direction of second component 310b as displaceable member 200 returns to a non-depressed position. Similarly, the contact surfaces of second component 210b and second component 310b result in lateral movement of second component 310b in the direction of first component 310a as displaceable member 200 returns to a non-depressed position. By allowing movement of first component 310a and second component 310b in the direction of one another, plunger engagement surface 312a and plunger engagement surface 312b threadably engage the threads of the plunger. This allows the user to advance/retract the plunger in a threaded fashion while minimizing non-threaded movement of the plunger relative to release mechanism 20. The juxtaposition of the engagement surfaces of first component 210a and second component 310a and the engagement surfaces of second component 210b and second component 310b during movement of displaceable member 200 will be discussed in greater detail with reference to FIGS. 6A-6C.

Figure 6A:
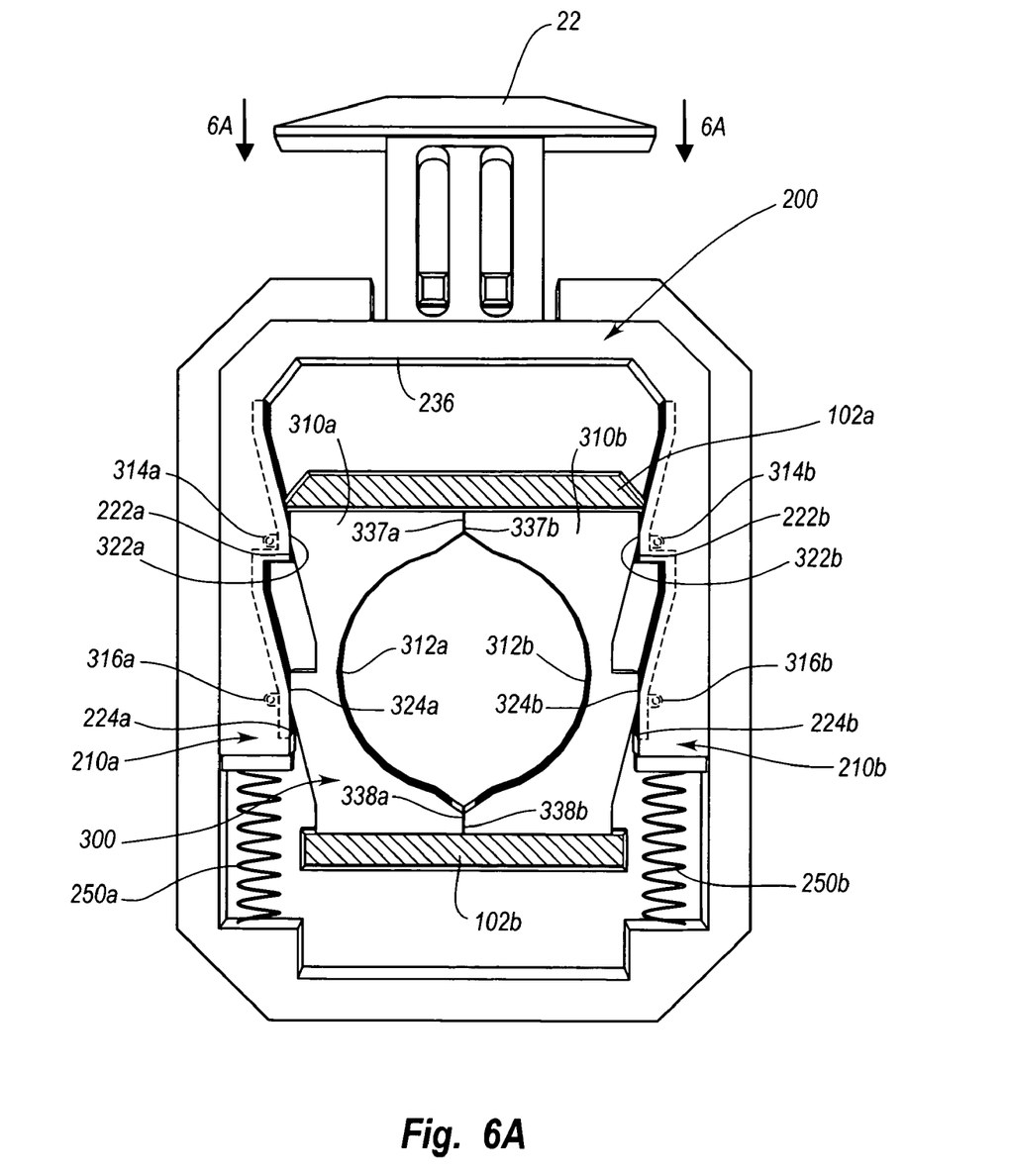
FIG. 6A is a top cross sectional view of the collar of FIG. 1 illustrating the position of the displaceable member relative to the engagement mechanism in which the engagement mechanism engages the plunger in a threaded fashion, according to one embodiment of the present invention.

FIG. 6A is a top cross sectional view of collar 1 illustrating the juxtaposition of displaceable member 200 relative to engagement mechanism 300 when displaceable member 200 is in a non-depressed position. In the illustrated embodiment, button portion 22 is integrally coupled to displaceable member 200 such that when button portion 22 is stationary, displaceable member 200 is stationary.

When displaceable member 200 is not depressed, first component 310a and second component 310b of engagement mechanism 300 are touching. This allows plunger engagement surface 312a and plunger engagement surface 312b to threadably engage the threads of the plunger (not shown). In the embodiment, first front surface 337a of first component 310a contacts first front surface 337b of second component 310b. Second front surface 338a of first component 310a also contacts second front surface 338b of second component 310b.

FIG. 6A also illustrates the juxtaposition of first projection 102a and second projection 102b relative to first component 310a and second component 310b of engagement mechanism 300. First projection 102a and second projection 102b are positioned on the top and bottom ends of first component 310a and second component 310b to minimize movement of first component 310a and second component 310b in the direction toward, or away from, button portion 22. As a result, when displaceable member 200 is depressed in the direction of directional arrows 6a-6a, movement of first component 310a and second component 310b in the direction of directional arrows 6a-6a is minimized.

First component 210a engages first component 310a in a manner that maintains contact between first component 210a and first component 310a. When displaceable member 200 is not depressed, upper horizontal contact surface 222a is in contact with upper horizontal contact surface 322a. Upper horizontal contact surface 224a is in contact with upper horizontal contact surface 324a. The horizontal contact surfaces 222a, 224a, 322a, and 324a provide planar and reliable contact surfaces which maintain the juxtaposition of first component 210a relative to first component 310a in the absence of outside forces being exerted on displaceable member 200. By utilizing horizontal contact surfaces, inadvertent movement of displaceable member 200 relative to engagement mechanism 300 is minimized.

As discussed with reference to FIG. 5, the coupling of first component 210a and first component 310a is maintained by use of flange member 314a and flange member 316a. The interaction between flange members 314a and 316a and the relief surface of recess 211a causes lateral displacement of first component 310a in the lateral direction as first component 210a moves in the direction of directional arrows 6a-6a. In the illustrated embodiment, first component 310a and second component 310b are positioned adjacent to one another. This is due to the fact that upper horizontal contact surfaces 322a and upper horizontal contact surface 324a contact upper horizontal contact surface 322a and upper horizontal contact surfaces 224a. In other words, the portions of first component 210a having the greatest amount of inward projection (upper horizontal contact surface 222a and upper horizontal contact surface 224a) are in contact with the portions of first component 310a having the greatest outward lateral displacement (upper horizontal contact surface 322a and upper horizontal contact surface 324a). The result is that first component 310a is biased to its greatest displacement in the direction of second component 310b.

Second component 210b engages second component 310b in a manner that maintains contact between second component 210b and second component 310b. When displaceable member 200 is not depressed, upper horizontal contact surface 222b is in contact with upper horizontal contact surface 322b. Upper horizontal contact surface 224b is in contact with upper horizontal contact surface 324b. The horizontal contact surfaces 222b, 224b, 322b, and 324b provide planar and reliable contact surfaces which maintain the juxtaposition of second component 210b relative to second component 310b in the absence of outside forces being exerted on displaceable member 200. By utilizing horizontal contact surfaces, inadvertent movement of displaceable member 200 relative to engagement mechanism 300 is minimized.

The coupling of second component 210b and second component 310b is maintained by use of flange member 314b and flange member 316b. The interaction between flange members 314a and 316b and the relief surface of recess 211b causes lateral displacement of second component 310b in the lateral direction as second component 210b moves in the direction of directional arrows 6a-6a. In the illustrated embodiment, second component 310b and first component 310a are positioned adjacent to one another. This is due to the fact that upper horizontal contact surfaces 322b and upper horizontal contact surface 324b contact upper horizontal contact surface 222b and upper horizontal contact surfaces 224b. In other words, the portions of second component 210b having the greatest amount of inward projection (upper horizontal contact surface 222b and upper horizontal contact surface 224b) are in contact with the portions of second component 310b having the greatest outward lateral displacement (upper horizontal contact surface 322b and upper horizontal contact surface 324b). The result is that second component 310b is biased to its greatest displacement in the direction of first component 310a.

In the illustrated embodiment, there is also shown spring members 250a, b. Spring members 250a, b contact spring member engagement portions 237a, b. Spring member engagement portion 237a of first component 210a is contacted by spring member 250a resulting in a compressive force being exerted on first component 210a in the direction opposite directional arrows 6a-6a. Spring member engagement portion 237b of second component 210b is contacted by spring member 250b resulting in a compressive force being exerted in the direction opposite directional arrow 6a-6a. Spring members 250a, b minimize inadvertent movement of displaceable member 200 in direction of directional arrows 6a-6a. A predetermined amount of compressive force is required to overcome the compressive force exerted by spring members 250a, b on first component 210a and second component 210b. Once the predetermined amount of compressive force is exceeded, displaceable member 200 begins to move in the direction of the directional arrow 6a-6a. As will be appreciated by those skilled in the art, a variety of types and configurations of resilient members can be utilized in place of the spring members illustrated in FIG. 6A.

Figure 6B:
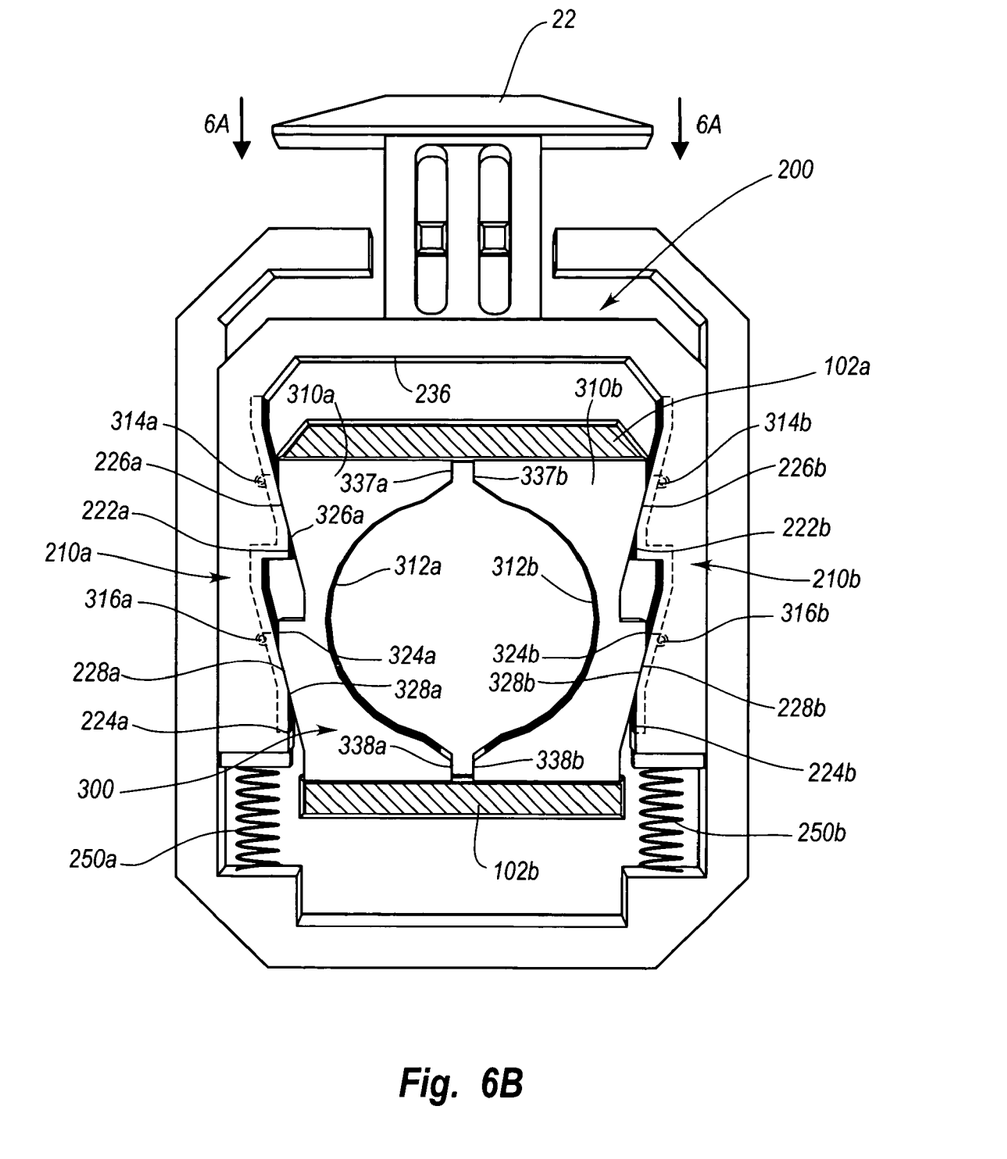
FIG. 6B is a top cross sectional view of the collar of FIG. 1 illustrating the juxtaposition of the displaceable member relative to the engagement mechanism when the displaceable member is partially depressed.

FIG. 6B illustrates collar 1 in which displaceable member 200 has begun to move in the direction of directional arrows 6a-6a. In the illustrated embodiment, a sufficient compressive force is exerted on displaceable member 200 in the direction of the directional arrow 6a-6a to overcome the resistive force provided by spring members 250a, b. In the illustrated embodiment, it can be seen that as displaceable member 200 moves in the direction of directional arrow 6a-6a, first component 210a and second component 210b are displaced relative to first component 310a and second component 310b.

In the embodiment, upper horizontal contact surface 222a is moving past upper horizontal contact surface 322a and first ramp surface 226a is positioned adjacent upper horizontal contact surface 322a. Similarly, upper horizontal contact surface 224a is moving past upper horizontal contact surface 324a and second ramp surface 228a is positioned adjacent upper horizontal contact surface 324a. Flange members 314a and 316a contact the relief surface of recess 211a (not shown) such that additional movement of first component 210a in the direction of directional arrow 6a-6a will result in additional movement of upper horizontal contact surface 222a causing first ramp surface 226a to move along the length of first ramp surface 326a.

Similarly, movement of first component 210a in the direction of directional arrows 6a-6a will result in additional movement of upper horizontal contact surface 224a causing second ramp surface 228a to move along the length of second ramp surface 328a. Movement of first ramp surface 226a along the length of first ramp surface 326a and movement of second ramp surface 228a along the length of second ramp surface 328a results in lateral movement of first component 310a in the direction away from second component 310b.

In the illustrated embodiment, upper horizontal contact surface 222b is moving past upper horizontal contact surface 322b and first ramp surface 226b is positioned adjacent upper horizontal contact surface 322b. Similarly, upper horizontal contact surface 224b is moving past upper horizontal contact surface 324b and second ramp surface 228b is positioned adjacent upper horizontal contact surface 324b. Flange member 314b and 316b contact the relief surface of recess 211b (not shown) such that additional movement of second component 210b in the direction of directional arrow 6a-6a will result in additional movement of upper horizontal contact surface 222b causing first ramp surface 226b to move along the length of first ramp surface 326b.

Similarly, movement of second component 210b in the direction of directional arrow 6a-6a will result in additional movement of upper horizontal contact surface 224b causing second ramp surface 228b to move along the length of second ramp surface 328b. Movement of first ramp surface 226b along the length of first ramp surface 326b and movement of second ramp surface 228b along the length of second ramp surface 328b results in lateral movement of second component 310b in the direction away from first component 310a. In the illustrated embodiment, it can be seen that there is a small displacement between first component 310a and second component 310b resulting from lateral movement of first component 310a and second component 310b. As a result, front surface 337a no longer contacts first front surface 337b and second front surface 338a no longer contacts second front surface 338b.

Figure 6C:
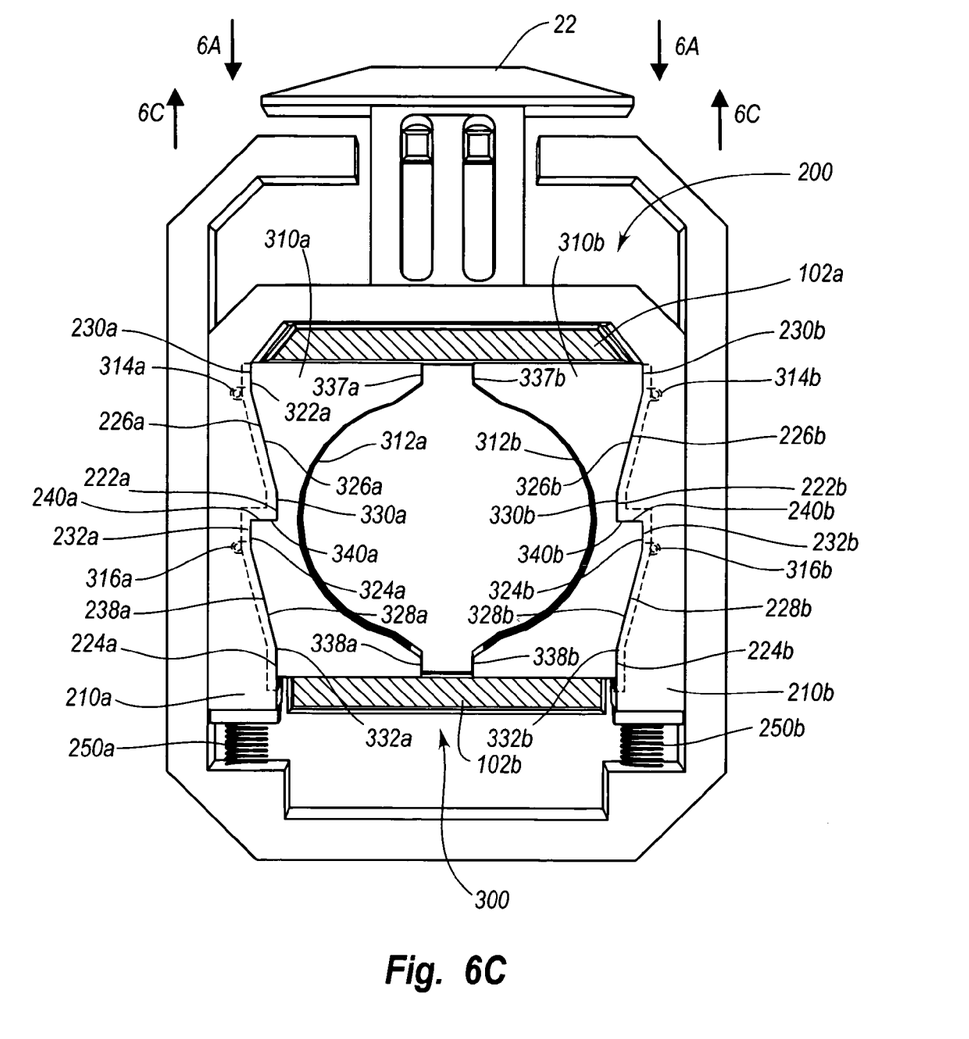
FIG. 6C is a top cross sectional view of the collar of FIG. 1 illustrating the juxtaposition of the displaceable member relative to the engagement mechanism allowing the user to advance/retract the plunger in a non-threaded fashion.

FIG. 6C illustrates the juxtaposition of engagement mechanism 300 relative to displaceable member 200 when displaceable member 200 is depressed to its fullest extent. In the illustrated embodiment, button portion 22 is fully depressed such that a second projection contact surface 236 of displaceable member 200 is in contact with second projection 102b effectively limiting movement of displaceable member 200 in the direction of directional arrows 6a-6a.

In the illustrated embodiment, first component 310a is positioned at its greatest lateral displacement away from second component 310b. First front surface 337a and second front surface 338a are positioned at their greatest displacement from first front surface 337b and second front surface 338b. In this position, plunger engagement surfaces 312a and 312b no longer threadably engage the threads of the plunger (not shown) allowing a user to advance/retract the plunger in a non-threaded fashion.

The juxtaposition of first component 310a and second component 310b relative to first component 210a and second component 210b represents a second position in which the release mechanism 200 engages the engagement mechanism 300 utilizing one or more ramps. In the illustrated embodiment, lower horizontal contact surface 230a is in contact with upper horizontal contact surface 322a. First ramp surface 226a is in contact with first ramp surface 326a. Upper horizontal contact surface 222a is in contact with lower horizontal contact surface 330a. Lower horizontal contact surface 232a is in contact with upper horizontal contact surface 324a. Second ramp surface 228a is in contact with second ramp surface 328a. Upper horizontal contact surface 224a is in contact with lower horizontal contact surface 332a. Additionally, stop surface 240a of first component 210a is in contact with stop surface 340a of first component 310a. Stop surface 240a and stop surface 340a prevent additional movement of displaceable member 200 in the direction of directional arrows 6a-6a.

As previously discussed, flange members 314a and 316a maintain a close contact between first component 210a and first component 310a. As a result, when displaceable member is in the illustrated depressed position, flange member 314a and flange member 316a position upper horizontal contact surface 322a adjacent lower horizontal contact surface 230a. Because the portions of first component 210a having the greatest inward projection (upper horizontal contact surface 222a and upper horizontal contact surface 224a) are positioned adjacent the portions of first component 310a having the least amount of lateral projection (lower horizontal contact surface 330a and lower horizontal contact surface 332a); and because the portions or first component 310a having the greatest lateral displacement (upper horizontal contact surface 322a and upper horizontal contact surface 324a) are positioned adjacent the portions of first component 210a having the least amount of inward projection (lower horizontal contact surface 230a and lower horizontal contact surface 232a) first component 310a is moved to a lateral displacement furthest from second component 310b.

In the illustrated embodiment, lower horizontal contact surface 230b is in contact with upper horizontal contact surface 322b. First ramp surface 226b is in contact with first ramp surface 326b. Upper horizontal contact surface 222b is in contact with lower horizontal contact surface 330b. Lower horizontal contact surface 232b is in contact with upper horizontal contact surface 324b. Second ramp surface 228b is in contact with second ramp surface 328b. Upper horizontal contact surface 224b is in contact with lower horizontal contact surface 332b. Additionally, stop surface 240b of second component 210b is in contact with stop surface 340b of second component 310b. Stop surface 240b and stop surface 340b prevent additional movement of displaceable member 200 in the direction of directional arrows 6a-6a.

As previously discussed, flange members 314b and 316b maintain close contact between second component 210b and second component 310b. As a result, when displaceable member 200 is in the illustrated depressed position, flange member 314b and flange member 316b position upper horizontal contact surface 322b adjacent lower horizontal contact surface 230b. Because the portions of second component 210b having the greatest inward projection (upper horizontal contact surface 222b and upper horizontal contact surface 224b are positioned adjacent the portions of second component 310b having the least amount of lateral projection (lower horizontal contact surface 330b and lower horizontal contact surface 332b); and because the portions of second component 310a having the greatest lateral displacement (upper horizontal contact surface 322b and upper horizontal contact surface 324b) are positioned adjacent the portions of second component 210b having the least amount of inward projection (lower horizontal contact surface 230b and lower horizontal contact surface 232b) second component 310b is moved to a lateral displacement furthest from first component 310a.

In the illustrated embodiment, a predetermined amount of force is required to maintain the compressed configuration of spring members 250a and 250b. When the force exerted on displaceable member 200 and/or button portion 22 is no longer sufficient to overcome the force exerted by spring members 250a and 250b on displaceable member 200, displaceable member 200 will move in the direction of directional arrows 6c-6c. The ramp configuration of first ramp surface 226a relative to first ramp surface 326a and second ramp surface 228a relative to second ramp surface 328a will force first component 310a laterally in the direction of second component 310b when displaceable member 200 moves in the direction of directional arrows 6c-6c. The ramp configuration of first ramp surface 226a, second ramp surface 228a and first ramp surface 326a and second ramp surfaced 328a encourages such lateral movement of first component 310a subsequent to movement of displaceable member 200. Additionally, the ramp configuration reduces the amount of force required to result in such lateral displacement of first component 310a.

The ramp configuration of first ramp surface 226b relative to first ramp surface 326b and second ramp surface 228b relative to second ramp surface 328b will force second component 310b laterally in the direction of first component 310a when displaceable member 200 moves in the direction of directional arrows 6c-6c. The ramp configuration of first ramp surface 226b, second ramp surface 228b, first ramp surface 326b, and second ramp surfaced 328b encourages such lateral movement of second component 310b subsequent to movement of displaceable member 200. Additionally, the ramp configuration reduces the amount of force required to result in such lateral displacement of second component 310b. As a result the amount of compressive force exerted by spring members 250a and 250b on first component 210a and second component 210b is sufficient to result in lateral movement of first component 310a and second component 310b.

As will be appreciated by those skilled in the art, a variety of types and configurations of release mechanisms can be utilized without departing from the scope and spirit of the present invention. For example in one embodiment, the release mechanism utilizes an integrated displaceable member and engagement mechanism. In another embodiment, the engagement mechanism comprises a portion of the housing. In another embodiment, a single ramp surface is utilized with respect to the displaceable member and an additional ramp surface is utilized with respect to the engagement mechanism. In another embodiment, the engagement mechanism utilizes a single movable engagement component. In another embodiment, the displaceable member is displaced utilizing something other than a button portion.

Figure 7A:
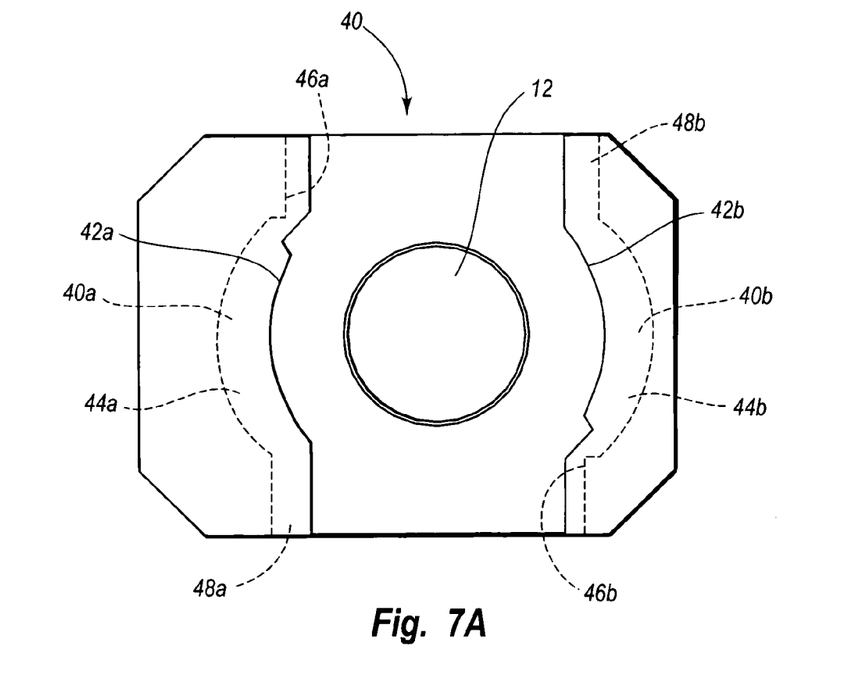
FIGS. 7A and 7B illustrate a sleeve for attaching or detaching the collar from a syringe device according to one embodiment of the present invention.
Figure 7B:
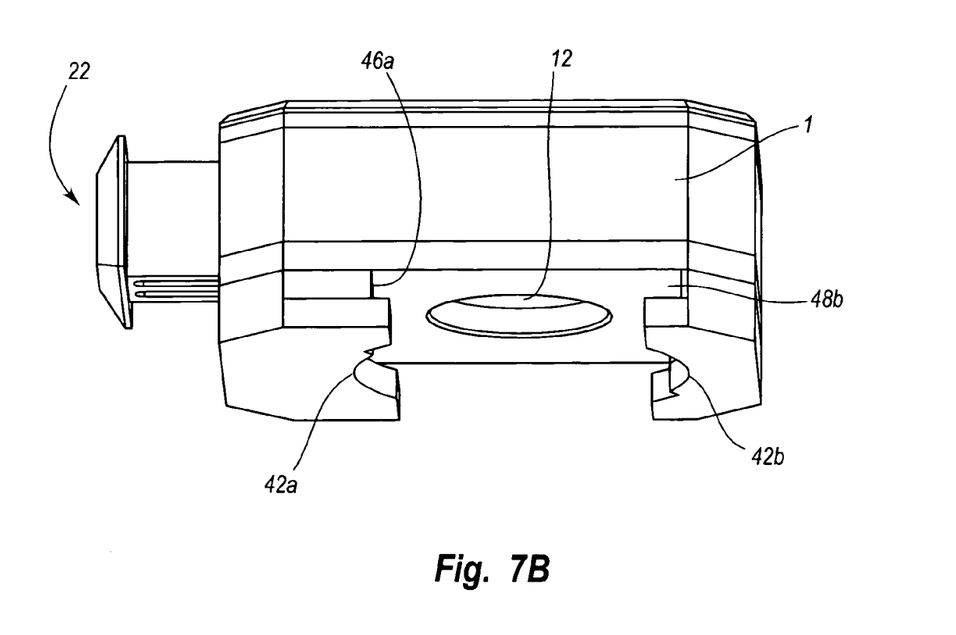

FIGS. 7A and 7B illustrates one presently preferred embodiment of a mechanism for selectively coupling and uncoupling collar 1 to/from flanges or finger rests commonly provided adjacent the proximal end of a syringe barrel. In the illustrated embodiment the coupling mechanism comprises a sleeve 40, formed in the bottom of collar 1, for selectively coupling and decoupling collar 1 to/from syringe 50. Sleeve 40 has an internal relief, the configuration of which is illustrated in hidden lines in FIG. 7A. Sleeve 40 comprises a first sleeve 40a and a second sleeve 40b, forming a transverse slot through the middle of the bottom surface of collar 1, bounded on either side by first and second sleeves 40a and 40b. First sleeve 40a comprises a lip 42a, a recess 44a, a projection 46a, and a void 48a. Similarly, second sleeve 40b comprises a lip 42b, a recess 44b, a projection 46b, and a void 48b. As described in additional detail below, lips 42a and 42b provide overhangs for securing the syringe barrel flange within voids 48a and 48b. Recesses 44a and 44b are positioned beneath lips 42a and 42b such that lips 42a and 42b extend further in the direction of aperture 12 than recesses 44a and 44b. As described in additional detail below, recesses 44a and 44b are adapted to accommodate the syringe barrel flanges with lips 42a and 42b covering the flanges.

Projections 46a and 46b are positioned laterally at one side of recesses 44a and 44b, respectively. Projections 46a and 46b contact the syringe barrel flange to prevent rotation of collar 1 past a given point. Voids 48a and 48b are positioned on the side of recesses 44a and 44b, respectively, opposite projections 46a and 46b, respectively. Voids 48a and 48b accommodates the syringe barrel flanges when the collar 1 is being coupled to the syringe. Additionally, voids 48a and 48b allow the user to remove the collar from the syringe barrel flange by allowing the flange to be twisted off collar 1 and exit through voids 48a and 48b.

Figure 8A:
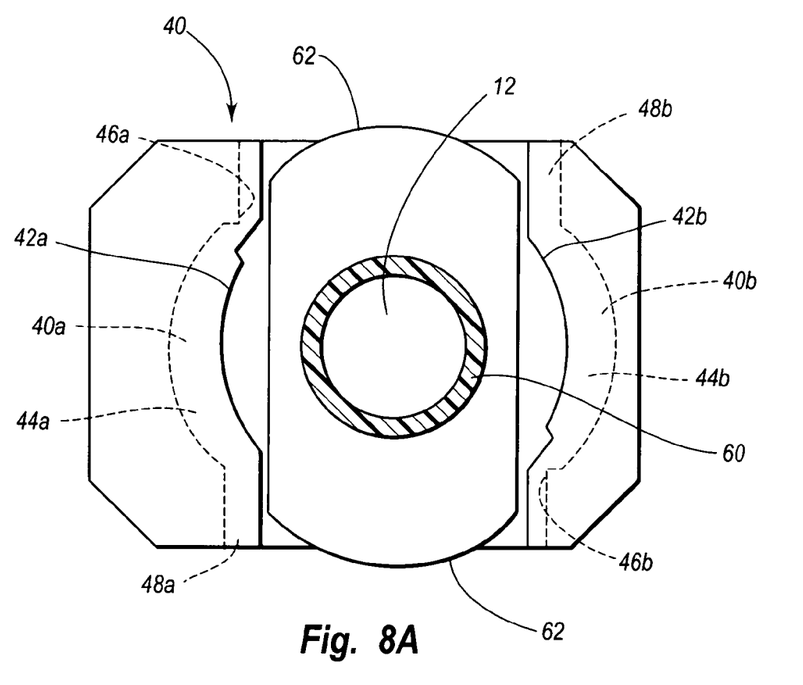
FIGS. 8A and 8B further illustrate the manner in which the collar is coupled to a syringe device according to one embodiment of the present invention.
Figure 8B:
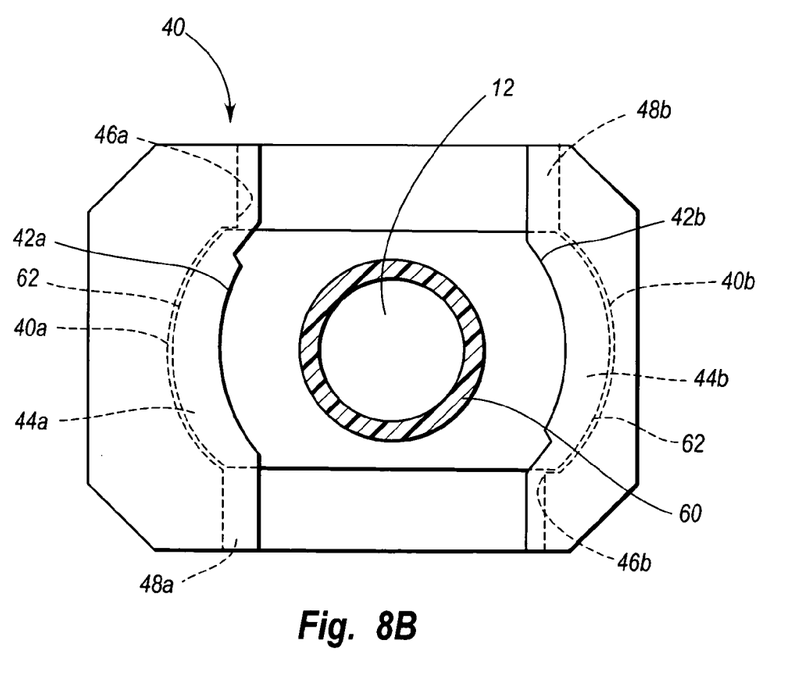

As illustrated in FIGS. 8A-C, sleeve 40 and the recesses formed therein are configured and dimensioned to receive the flanges 62 of an inflation syringe barrel 60 therein. To couple collar 1 to syringe 50, collar 1 rotated relative to syringe barrel 60 until the transverse slot formed between sleeves 40a and 40b is aligned with the flanges or finger rests 62 of syringe barrel 60, as depicted in FIG. 8A. Once so aligned, then collar 1 is lowered onto the proximal end of syringe barrel 60. This lowering is preferable accomplished by actuating release mechanism 20 to decouple collar 1 from the threads of plunger 70 and then lowering collar 1 onto the proximal end of syringe barrel 60. Then, once housing 10 of collar 1 is placed over proximal end of syringe barrel 60 to the point where the bottom surface of housing 10 contacts the proximal surface of flanges or finger rests 62 of syringe barrel 60, collar 1 and/or syringe barrel 60 are rotated relative to one another by 90 degrees of rotation and until the flanges 62 are positioned within recesses 44a and 44b, as depicted in FIG. 8B. In this position, collar 1 is securely coupled to the flanges 62 of syringe barrel 60 so as to prevent movement of collar 1 relative to syringe barrel 60 in a longitudinal direction.

Collar 1 may also be selectively decoupled from the proximal end of syringe barrel 60 in a similar fashion, albeit in reverse order. As discussed previously, decoupling of collar 1 from syringe barrel 60 allows for quick removal of collar 1 and syringe plunger 70 from syringe barrel 60 and for convenient backloading of material into the interior of syringe barrel 60 through its open proximal end.

As will be appreciated by those skilled in the art, a variety of types and configurations of sleeves can be utilized without departing from the scope and spirit of the present invention. For example in one embodiment, the sleeve is threadably coupled to the syringe. In another embodiment, another type of coupling mechanism is utilized to allow the user to selectively couple and decouple the collar from the syringe. The sleeve is one example of a coupler mechanism.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An improved quick release apparatus intended for use with a high pressure injection syringe for medical procedures, such as the injection of contrast media, wherein the syringe includes an elongate hollow cylindrical barrel and an elongate plunger configured to be slidingly received within and to engage the interior of the barrel, the barrel having an interior defined by an interior wall, a proximal end through which the material to be injected can be loaded into the syringe, a distal end through which the material to be injected is expressed, and a pair of enlarged, diametrically opposed flanges extending radially from opposite sides of the proximal end of the barrel, and the plunger having an elastomeric piston tip at a distal end configured to sealingly engage the inner wall of the barrel, an enlarged actuating portion at its proximal end configured to be manually manipulated by a medical professional in order to express from the syringe the material to be injected, and an elongate threaded shaft extending between the piston tip and the actuating portion, the quick release apparatus comprising:

a housing having a central bore extending therethrough, the bore having a diameter greater than the external diameter of the threads of the threaded shaft;

a coupler mechanism comprising a sleeve which defines one or more recesses having a dimension to receive one or more flanges of the proximal end of the barrel of the syringe, the coupler mechanism having a first operating position in which the one or more flanges are positioned within the one or more recesses of the sleeve to securely couple the housing to the proximal end of the syringe barrel and a second operating position in which the one or more flanges are not positioned in the one or more recesses of the sleeve in which the housing can be released and removed from the proximal end of the syringe barrel, such that movement of the housing and the barrel relative to one another in a direction parallel to the longitudinal axis of the barrel is prevented when the coupler is in the first operating position and the housing is coupled to the proximal end of the barrel, and when the coupler is in the second operating position the housing is configured to be selectively removed from the barrel to facilitate loading of the syringe through the proximal end of the barrel, wherein the coupler mechanism is configured such that a practitioner can move the coupler mechanism between the first position and the second position in the course of an injection procedure to remove the housing from the barrel of the syringe and to load the syringe through the proximal end of the barrel during the course of the procedure;

a moveable member located within the housing for selectively coupling the housing to the threads of the threaded shaft, the moveable member having threads complementary of and configured to engage at least a portion of the threads of the threaded shaft, the threaded portion being moveable between a first position in which the threads of the moveable member engage at least a portion of the threads of the threaded shaft such that the plunger can only be advanced and retracted relative to the barrel by rotating the plunger and the barrel relative to one another, and a second position in which the threads of the moveable member do not engage the threads of the threaded shaft so that the plunger can only be advanced and retracted relative to the barrel by pushing or pulling the plunger and barrel relative to one another in the longitudinal direction; and an actuating button accessible to the exterior of the housing and mechanically coupled to the moveable member, for selectively moving the moveable member between the first and second positions of the moveable member.

2. The quick release apparatus set forth in claim 1, wherein the sleeve of the coupler comprises at least one recess configured to receive the flanges of the barrel in mating relationship.

3. The quick release apparatus set forth in claim 1, wherein the moveable member is biased to rest in the first position so that the threads of the moveable member engage the threads of the threaded shaft except when the actuating button is manually depressed.

4. The quick release apparatus set forth in claim 3, wherein the actuating button includes a displaceable member configured to engage the first component and the second component.

5. The quick release apparatus set forth in claim 4, wherein a user depresses the actuating button to displace the first component and second component from the elongate threaded shaft to allow the user to advance or retract the plunger in a threadless fashion.

6. The quick release apparatus set forth in claim 5, wherein the actuating button automatically returns to a non-depressed position and the first component and the second component automatically threadably engage the elongate threaded shaft when the user releases the actuating button.

7. The quick release apparatus set forth in claim 1, wherein the movable member comprises a first component and a second component positioned on opposite sides of the elongate threaded shaft of the plunger.

8. The quick release apparatus set forth in claim 7, wherein one or both of the first component and the second component have an internal threaded surface which threadably interact with the elongate threaded shaft of the plunger.

9. The quick release apparatus set forth in claim 8, wherein when the movable member is in the first position the first component and the second component engage the elongate threaded shaft of the plunger and wherein when the movable member is in the second position one or both of the first component and the second component are displaced relative to the first position such that one or both of the first portion and the second portions do not engage the elongate threaded shaft.

10. A collar for use with an inflation device, the inflation device having a pressure gauge for monitoring the amount of pressurization in the inflation device, the collar comprising:

a release mechanism having a first position permitting a plunger of the inflation device to be engaged and a second position allowing the plunger to advance or retract the plunger in a non-threaded fashion, wherein the release mechanism comprises;

an enlargement mechanism having a first moveable component and a second moveable component positioned on opposing sides of a threaded shaft of the plunger, the first moveable component and second moveable component configured to selectively engage and disengage threads of the threaded shaft of the plunger;

a depressible button accessible from the exterior of release mechanism and mechanically coupled to the engagement mechanism, the depressible button operably connected to the engagement mechanism such that the depressible button is configured to selectively move the first moveable component in a direction opposite the second moveable component and move the second moveable component in a direction opposite the first moveable component such that when the depressible button is in a released position the first moveable component and the second moveable component cooperatively engage the threaded shaft of the plunger and when the depressible button is in a depressed position the first moveable component and the second moveable component cooperatively engage the threaded shaft of the plunger; and one or more resilient members which minimize inadvertent movement of the first moveable component and the second moveable component, wherein the one or more resilient members exert a resilient force relative to one or more of the engagement mechanism and the depressible button to maintain the first moveable component and the second moveable component in an engaged position in which the threads of the first moveable component and the second moveable component engage at least a portion of the threads of the threaded shaft.

11. The collar of claim 10, wherein the first position of the release mechanism comprises on non-depressed position and the second position comprises a depressed position.

12. The collar of claim 10, wherein the release mechanism further comprises a displaceable member that mechanically couples the depressible button to the engagement mechanism.

13. The collar of claim 12, wherein the displaceable member moves relative to the engagement mechanism.

14. The collar of claim 12, wherein a given amount of displacement is provided between first component and second component when the displaceable member is in the depressed position.

15. The collar of claim 14, wherein the displacement between the first component and the second component allows the plunger to move relative to the first component and the second component in a non-threaded fashion.

16. The collar of claim 15, wherein the first component is positioned adjacent the second component when the displaceable member is in a non-depressed position.

17. The collar of claim 16, wherein the plunger is threadably engaged by the engagement member when the first component is positioned adjacent the second component.

18. A collar for use with an inflation device, the inflation device having a pressure gauge for monitoring the amount of pressurization in the inflation device, the collar comprising:

a housing;

a release mechanism comprising;

an engagement mechanism for engaging a plunger of the inflation device, the plunger having a plurality of threads, wherein the engagement mechanism has a first component and a second component positioned on opposing sides of a threaded shaft of the plunger, the first component and second component configured to selectively engage and disengage the threads of the plunger;

a displaceable member having a first position permitting the plunger to be engaged and a second position allowing a user to advance or retract the plunger in a non-threaded fashion, wherein in the first position the displaceable member engages the engagement mechanism along a horizontal plane and wherein in the second position the displaceable member engages the engagement mechanism utilizing one or more ramp surfaces; and a sleeve for engaging a flange of the inflation device, wherein the configuration of the sleeve defines one or more recesses having a dimension to receive one or more flanges of the proximal end of the barrel of the syringe, the sleeve having a first operating position in which the one or more flanges are positioned within the one or more recesses of the sleeve to securely couple the housing to the proximal end of the syringe barrel and a second operating position in which the one or more flanges are not positioned in the one or more recesses of the sleeve in which the housing can be released and removed from the proximal end of the syringe barrel, such that movement of the housing and the barrel relative to one another in a direction parallel to the longitudinal axis of the barrel is prevented when the sleeve is in the first operating position and the housing is coupled to the proximal end of the barrel, and when the sleeve is in the second operating position the housing is configured to be selectively removed from the barrel to facilitate loading of the syringe through the proximal end of the barrel, wherein the sleeve is configured such that a practitioner can move the sleeve between the first position and the second position in the course of an injection procedure to remove the housing from the barrel of the syringe and to load the syringe through the proximal end of the barrel during the course of the procedure.

19. An improved quick release apparatus intended for use with a high pressure injection syringe for medical procedures, the quick release apparatus comprising:

a housing having a central bore extending therethrough, the bore having a diameter greater than an external diameter of a plunger of the high pressure injection syringe;

a release mechanism having a first position adapted to allow a user to incrementally advance and retract the plunger in a threaded fashion and a second portion adapted to allow the user to selectively advance and retract the plunger in a non-threaded fashion, wherein the release mechanism comprises:

a first moveable member and a second moveable member located within the housing for selectively coupling the housing to threads of a threaded shaft of the plunger, the first moveable member and second moveable member positioned on opposing sides of a threaded shaft of the plunger, a depressible button accessible from the exterior of the housing and mechanically coupled to the moveable member, the depressible button configured to selectively move the first moveable member and second moveable member between a first and a second position, one or more resilient members which minimize inadvertent movement of the first moveable member and second moveable member within the housing, wherein the one or more resilient members exert a resilient force relative to one or more of the first moveable member, the second moveable member, and the depressible button to maintain the first moveable member and second moveable member in an engaged position in which the threads of the first moveable member and second moveable member engage at least a portion of threads of a threaded shaft of the plunger, wherein a user exerts a predetermined amount of depressive force on the depressible button to overcome the resilient force exerted by the one or more resilient members to move the first moveable member and second moveable member from the engaged position in which the first moveable member and second moveable member engages the threads of the threaded shaft to a released position in which the threads of the first moveable member and second moveable member do not engage the threads of the threaded shaft, and wherein the first moveable member and second moveable member automatically returns to the released position, enabling the threads of the first moveable member and second moveable member to engage at least a portion of the threads of the threaded shaft, when the user releases the depressive force exerted on the depressible button such that the depressive force exerted on the button is no longer sufficient to overcome the compressive force exerted by the one or more resilient members on one or more of the first moveable member, the second moveable member, and the depressible button.

20. The collar of claim 19, wherein the position of the release mechanism allows the user to actuate the release mechanism and hold the syringe with a single hand.

21. The collar of claim 19, wherein depressing the depressible button actuates the release mechanism.

22. The collar of claim 19, wherein the release mechanism comprises a displaceable member and an engagement mechanism.

23. The collar of claim 22, wherein the displaceable member has a first position and a second position.

24. The collar of claim 23, wherein when the displaceable member is in the first position, the engagement mechanism engages the plunger in a threaded fashion.

25. The collar of claim 24, wherein when the displaceable member is in the second position, the engagement mechanism allows the user to advance or retract the plunger in a non-threaded fashion.

26. The collar of claim 25, wherein the first position of the displaceable member comprises a non-depressed position.

27. The collar of claim 26, wherein the second position of the displaceable member comprises a depressed position. of the collar.

* * * * *